US012721650B2

(12) United States Patent
Morrissette

(10) Patent No.: US 12,721,650 B2
(45) Date of Patent: Sep. 1, 2026

(54) INSTRUMENT ACCESS DEVICE WITH INTEGRATED TASK LIGHTING

(71) Applicant: Intuitive Surgical Operations, Inc., Sunnyvale, CA (US)

(72) Inventor: Tyler J. Morrissette, Niantic, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1054 days.

(21) Appl. No.: 17/514,999

(22) Filed: Oct. 29, 2021

(65) Prior Publication Data

US 2022/0133352 A1 May 5, 2022

Related U.S. Application Data

(60) Provisional application No. 63/107,317, filed on Oct. 29, 2020.

(51) Int. Cl.
*A61B 17/34* (2006.01)
*A61B 90/30* (2016.01)

(52) U.S. Cl.
CPC .......... *A61B 17/3423* (2013.01); *A61B 90/30* (2016.02); *A61B 2017/3445* (2013.01)

(58) Field of Classification Search
None
See application file for complete search history.

(56) References Cited

U.S. PATENT DOCUMENTS 4,711,630 A * 12/1987 Durr ...................... A61C 1/052 433/29
5,582,608 A * 12/1996 Brown ............... A61B 17/0231 606/4
5,672,168 A * 9/1997 de la Torre ........ A61B 17/3423 606/1
6,551,346 B2 * 4/2003 Crossley .............. A61N 5/0601 604/20
7,228,052 B1 * 6/2007 Lin ........................... F21K 9/27 362/555
7,489,396 B1 * 2/2009 Vrhel ...................... G01N 21/25 250/226
9,918,802 B2 * 3/2018 Coppersmith .......... F21V 29/70
2004/0127772 A1 * 7/2004 Ewers ..................... A61B 90/30 600/212
2006/0247498 A1 * 11/2006 Bonadio ............ A61B 17/3421 600/208

(Continued)

FOREIGN PATENT DOCUMENTS

CN 209358686 U * 9/2019
KR 913743 B1 * 8/2009 ......... A61B 17/3421

OTHER PUBLICATIONS

Vertut, J. and Coiffet, P., "Robot Technology: Teleoperation and Robotics Evolution and Development." English translation, Prentice-Hall, Inc., Inglewood Cliffs, NJ, USA 1986, vol. 3A, 332 pages.

*Primary Examiner* — Jan Christopher L Merene
(74) *Attorney, Agent, or Firm* — Schwegman, Lundberg & Woessner, P.A.

(57) ABSTRACT

A medical device includes means for covering the proximal opening of a wound retractor. The means for covering includes means for introducing one or more instruments through the means for covering and means for illuminating a zone adjacent the wound retractor.

13 Claims, 8 Drawing Sheets

(56) References Cited

U.S. PATENT DOCUMENTS

| | | | | |
|---|---|---|---|---|
| 2006/0247678 | A1* | 11/2006 | Weisenburgh | A61F 2/0063<br>606/205 |
| 2009/0036745 | A1* | 2/2009 | Bonadio | A61B 17/3498<br>600/208 |
| 2010/0008101 | A1* | 1/2010 | Bucher | F21S 41/141<br>362/565 |
| 2010/0063364 | A1* | 3/2010 | Bonadio | A61B 17/3423<br>600/208 |
| 2010/0081871 | A1* | 4/2010 | Widenhouse | A61B 17/3462<br>600/104 |
| 2010/0125172 | A1* | 5/2010 | Jayaraj | A61B 1/06<br>600/249 |
| 2010/0261974 | A1* | 10/2010 | Shelton, IV | A61B 17/3439<br>600/206 |
| 2011/0112371 | A1* | 5/2011 | Smith | A61B 17/3423<br>600/201 |
| 2013/0267787 | A1* | 10/2013 | Warnock | A61B 90/30<br>606/49 |
| 2014/0163326 | A1* | 6/2014 | Forsell | B25J 21/02<br>600/207 |
| 2014/0376897 | A1* | 12/2014 | Ranish | H01L 21/67115<br>392/416 |
| 2017/0071629 | A1* | 3/2017 | Patel | A61B 34/30 |
| 2017/0167670 | A1* | 6/2017 | Aliakseyeu | F21S 4/22 |
| 2018/0161203 | A1* | 6/2018 | Hopper | A61F 9/00 |
| 2021/0259537 | A1* | 8/2021 | Norton | A61B 17/3423 |
| 2022/0401125 | A1* | 12/2022 | Litke | A61B 17/0218 |

* cited by examiner

INSTRUMENT ACCESS DEVICE WITH INTEGRATED TASK LIGHTING

CLAIM OF PRIORITY

This application claims the benefit of priority under 35 U.S.C. § 119(e) to U.S. Patent Application Ser. No. 63/107,317, filed on Oct. 29, 2020, which is incorporated by reference herein in its entirety.

TECHNICAL FIELD

This document relates generally to medical devices, and more particularly, to devices and methods for illuminating different portions of a minimally invasive surgical site and/or different portions of devices used in such procedures.

BACKGROUND

Surgical systems, such as those employed for minimally invasive medical procedures, can include large and complex equipment to precisely control and drive relatively small tools or instruments. Such systems are sometimes referred to as a teleoperated controlled systems or robotic surgical systems. One example of a teleoperated controlled surgical system is the da Vinci® surgical system commercialized by Intuitive Surgical, Inc.

Various telesurgical system architectures exist. Some system architectures enable multiple (e.g., two, three, four, or more) surgical instruments to enter the body through a single body opening (surgical incision or natural orifice), and these systems are sometimes referred to as "single-port" systems (e.g., the da Vinci SP® surgical system commercialized by Intuitive Surgical, Inc.). Other system architectures enable multiple surgical instruments to enter the body individually at corresponding multiple locations, and these systems are sometimes referred to as "multi-port" systems (e.g., the da Vinci Xi® surgical system, commercialized by Intuitive Surgical, Inc.).

The access ports through which teleoperated systems deliver instruments to the body are typically sealed to maintain insufflation flow and pressure during the surgical procedure. Providing illumination of portions of such access port devices can assist clinicians (e.g., surgeons) with carrying out minimally invasive surgeries, whether conducted using a "single-port" telesurgical system architecture or a multi-port architecture.

SUMMARY

An example medical device includes means for covering the proximal opening of a wound retractor. The means for covering includes: means for introducing one or more instruments through the means for covering; and means for illuminating a zone adjacent the wound retractor.

An example method in accordance with this disclosure includes retracting an incision with a wound retractor, connecting an instrument access device to the wound retractor, the instrument access device being configured to seal a proximal opening of the wound retractor, and the instrument access device comprising an illumination device, and illuminating at least a portion of the retracted incision with the illumination device.

An instrument access device an envelope, a clamp, and an instrument seal assembly. The envelope includes a distal end, a proximal end, a cavity between the distal and proximal ends, and an opening at the proximal end. The clamp is coupled to the distal end and configured to be coupled to a wound retractor. The instrument seal assembly is coupled to the proximal end and configured to seal the proximal opening. The instrument seal assembly includes an illumination device configured to illuminate a zone on and/or within a perimeter of the clamp.

Each of these non-limiting examples can stand on its own or can be combined in various permutations or combinations with one or more of the other examples.

This Summary is intended to provide an overview of subject matter of the present patent application. It is not intended to provide an exclusive or exhaustive explanation of the invention. The detailed description is included to provide further information about various aspects of the inventive subject matter of the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
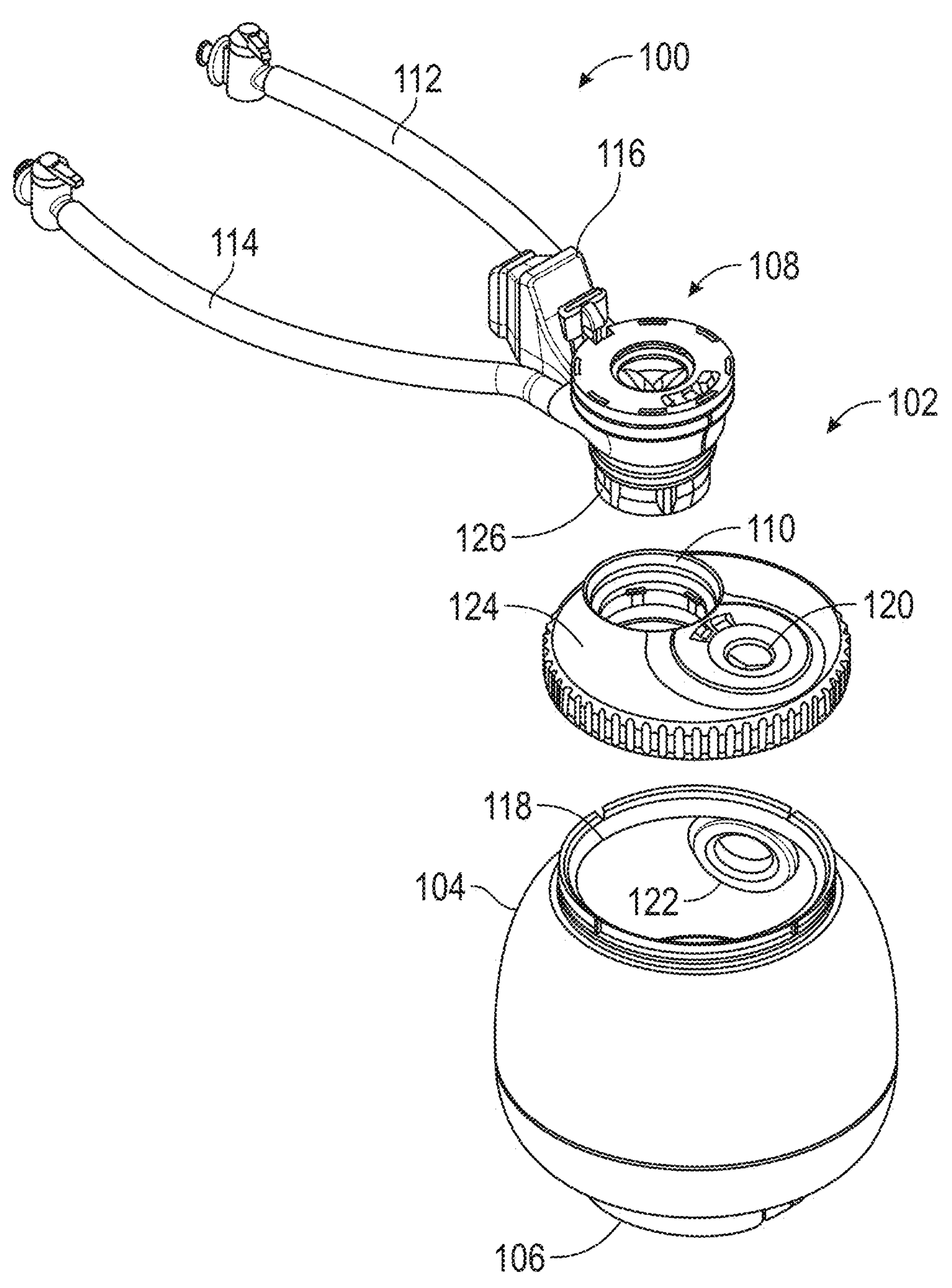
FIG. 1A is an exploded view of an example instrument access device in accordance with this disclosure.

Examples according to this disclosure are directed to instrument access devices with integrated task lighting to provide illumination to minimally invasive surgical sites, FIG. 1A is an exploded view of instrument access device 100 in accordance with this disclosure. In FIG. 1A, instrument access device 100 includes instrument seal assembly 102, envelope 104, and clamp 106. Instrument seal assembly 102 includes cannula assembly 108. Cannula assembly 108 is received in cannula port 110 of instrument seal assembly 102. Additionally, cannula assembly 108 includes insufflation lines 112 and 114, which are configured to carry insufflation gas through the lines and into/out of instrument access device 100, including into/out of envelope 104. Cannula assembly 108 also includes blade 116. Blade 116 affixes instrument access device 100 to an arm of a teleoperated surgical system.

Instrument seal assembly 102 is received in a proximal opening 118 of envelope 104. Instrument seal assembly 102 includes assistant port 120. Clamp 106 is received in a distal opening of envelope 104 and is configured to seal with and connect to a wound retractor in a surgical incision in the body wall of the patient. Envelope 104 includes an additional assistant port 122. Additionally, instrument seal assembly 102 includes base 124 and cannula assembly 108 includes cannula 126.

The access ports through which teleoperated systems deliver instruments to the body are typically sealed to maintain insufflation flow and pressure during the surgical procedure. In some cases, an access port device, which may include, for example, a wound retractor, a cannula received in the wound and wound retractor, and an entry guide received in the cannula, is disposed at the site of incision in the body of the patient. The seals that maintain insufflation pressure are included in the access port device and are thereby also located generally adjacent to the incision/surface of the body. In such situations, articulation of the instruments of the teleoperated system occurs just outside and above the incision site and the instrument end effectors are located inside the body below the incision and the outer surface of the body.

The end effectors that are manipulated by the surgeon in these types of procedures are located relatively deeply within the body of the patient. There are situations, however, where it may be necessary or advantageous to control the end effectors of the instruments at or very close to the surface of the body at the incision site. In such situations, the challenge is maintaining insufflation of the body cavity of the patient while also providing enough room for the arms of the instruments to articulate outside the body such that the instrument end effectors are located at or near the surface of the body.

To provide a sealed zone outside the body within which the instrument arms/shafts of a teleoperated surgical system may articulate, instrument access device 100 includes envelope 104, which is positioned between proximally located instrument seal assembly 102 and distally located wound retractor clamp 106. Instrument seal assembly 102 can be a multiple instrument single port access device, which is configured to accommodate and seal multiple surgical instruments through a single access port, for example, using a multi-instrument entry guide received in the cannula of cannula assembly 108. Instrument access device 100 is configured to receive an insufflation gas and to maintain insufflation pressure within a cavity in the body of a patient and to maintain insufflation pressure within the cavity of envelope 104. The pressurized and sealed envelope 104 provides an operating space for arms/shafts of multiple instruments of a teleoperated surgical system to articulate outside the body such that instrument end effectors are located at or near the surface of the body at the incision site of the wound retractor coupled to the instrument access device.

During minimally invasive surgeries, once the surgeon starts the procedure the operating room lights are dimmed (or nearly turned off) around the patient to prevent glare or stray light from obscuring the surgical view in the room monitors. As noted above, instrument access device 100 includes assistant ports 120 and 122. Assistant ports 120 and 122 can each be configured to receive and seal a manually operated instrument and can include a variety of types of seals including a cross-slit, duckbill, wiper, or septum seal. A bedside assistant that uses an assistant port like port 120 or 122 needs to quickly and safely introduce hand laparoscopic instruments through the port and into the patient. The assistant can, for example, pass suture, gauze, pull specimens, or other assist tasks via port 120. As described in more detail below, examples according to this disclosure can provide the beside assistant and/or the surgeon with task lighting, integrated into example instrument access devices in accordance with this disclosure, to provide the amount of light needed at the surgical site at which the access device is employed.

In examples, instrument access device 100 can include a mechanism that connects base 124 of instrument seal assembly 102 to cannula 126 of cannula assembly 108. The mechanism is configured to rotate assistant port 120 around cannula 126 without envelope 104 rotating about a central axis of the envelope 104. Thus, the mechanism allows assistant port 120 to rotate around cannula 126 without twisting envelope 104.

Figure 1B:
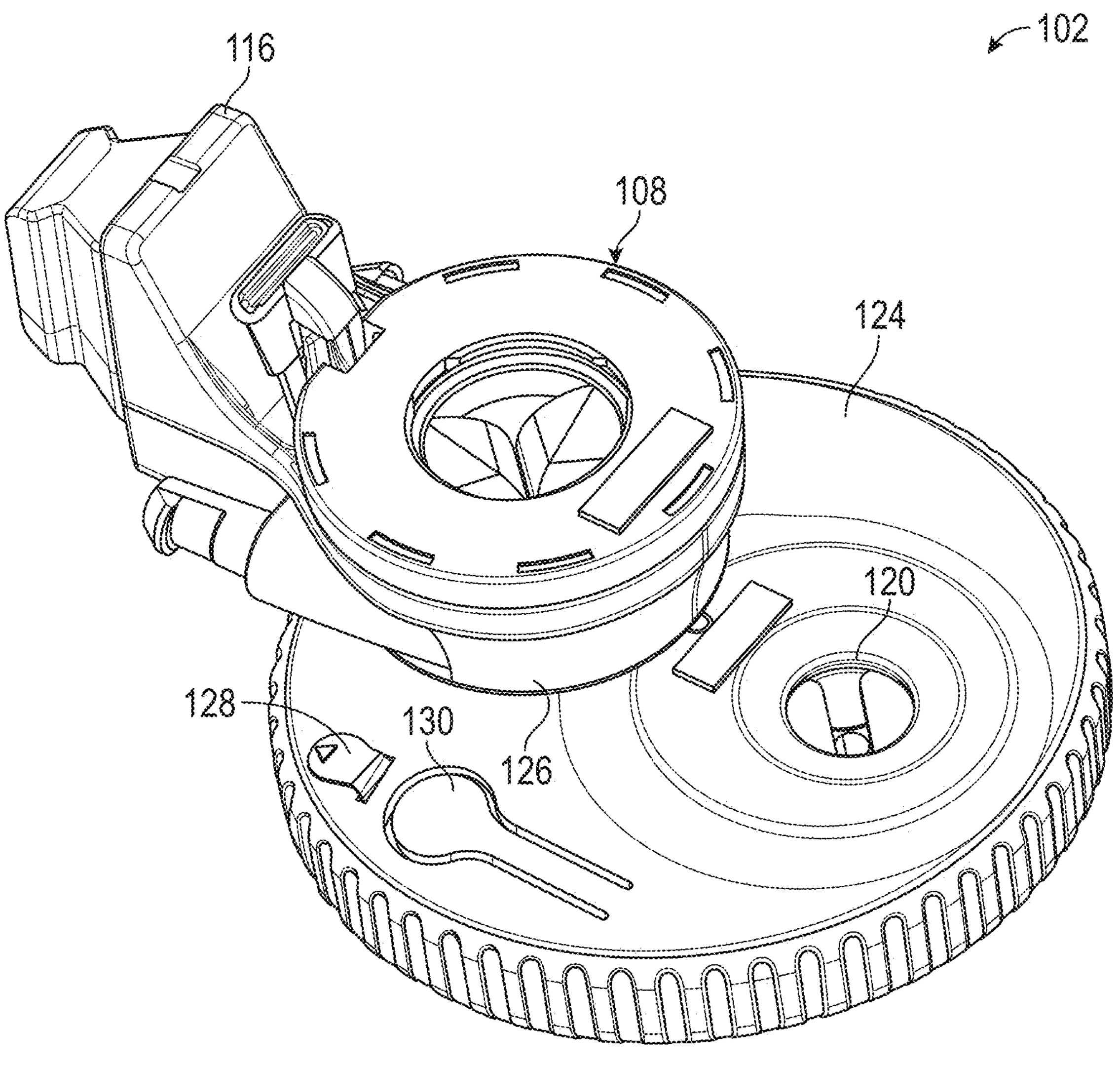
FIGS. 1B-1F depict different views of the example instrument seal assembly of the instrument access device of FIG. 1A including one or more integrated illumination devices.
Figure 1C:
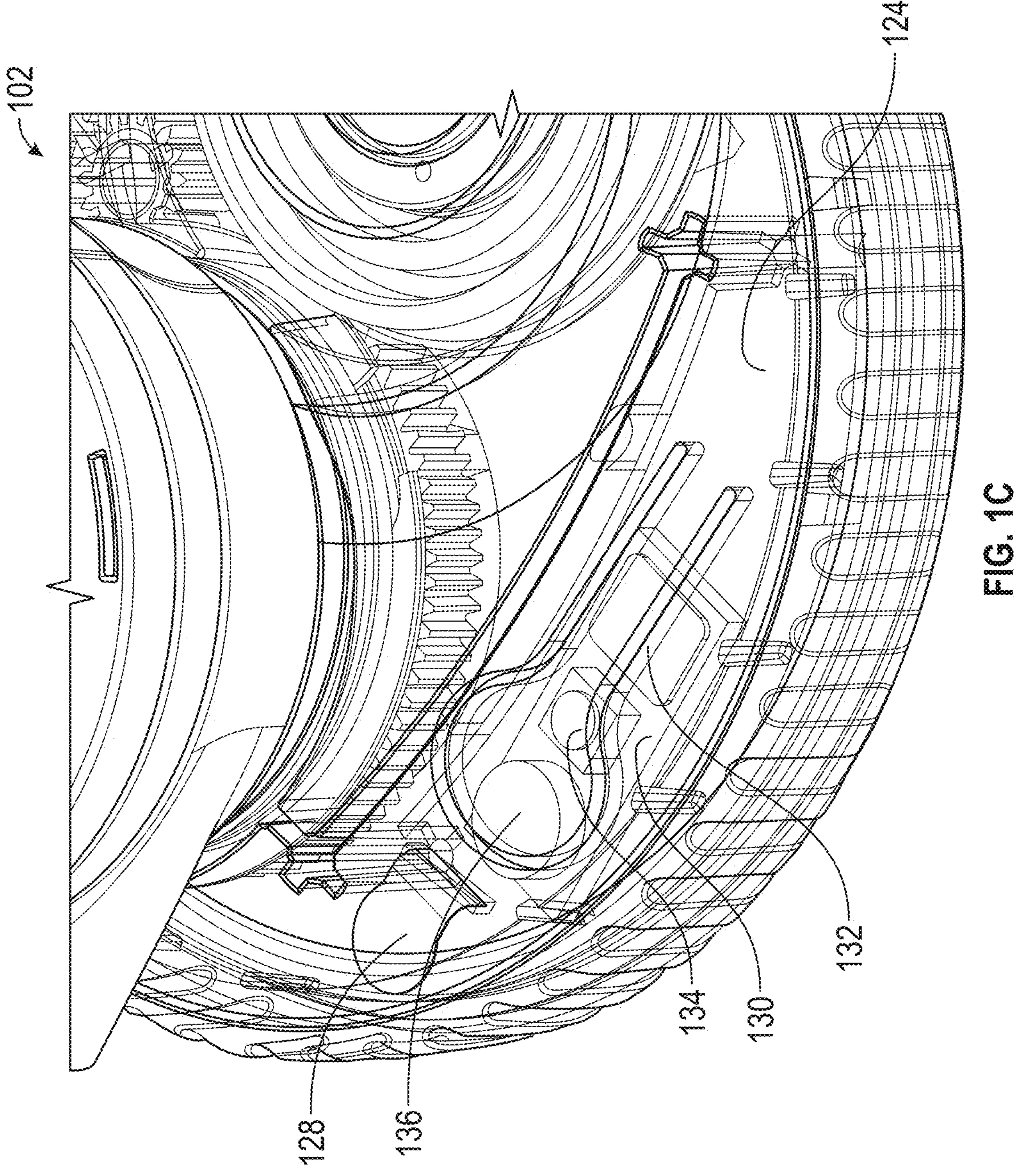
Figure 1D:
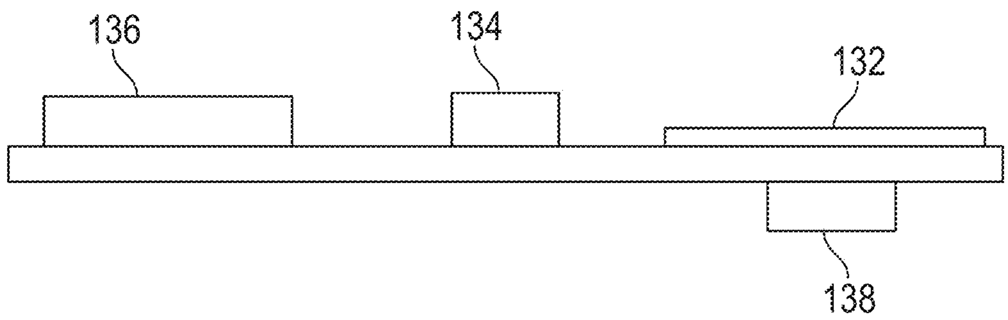
Figure 1E:
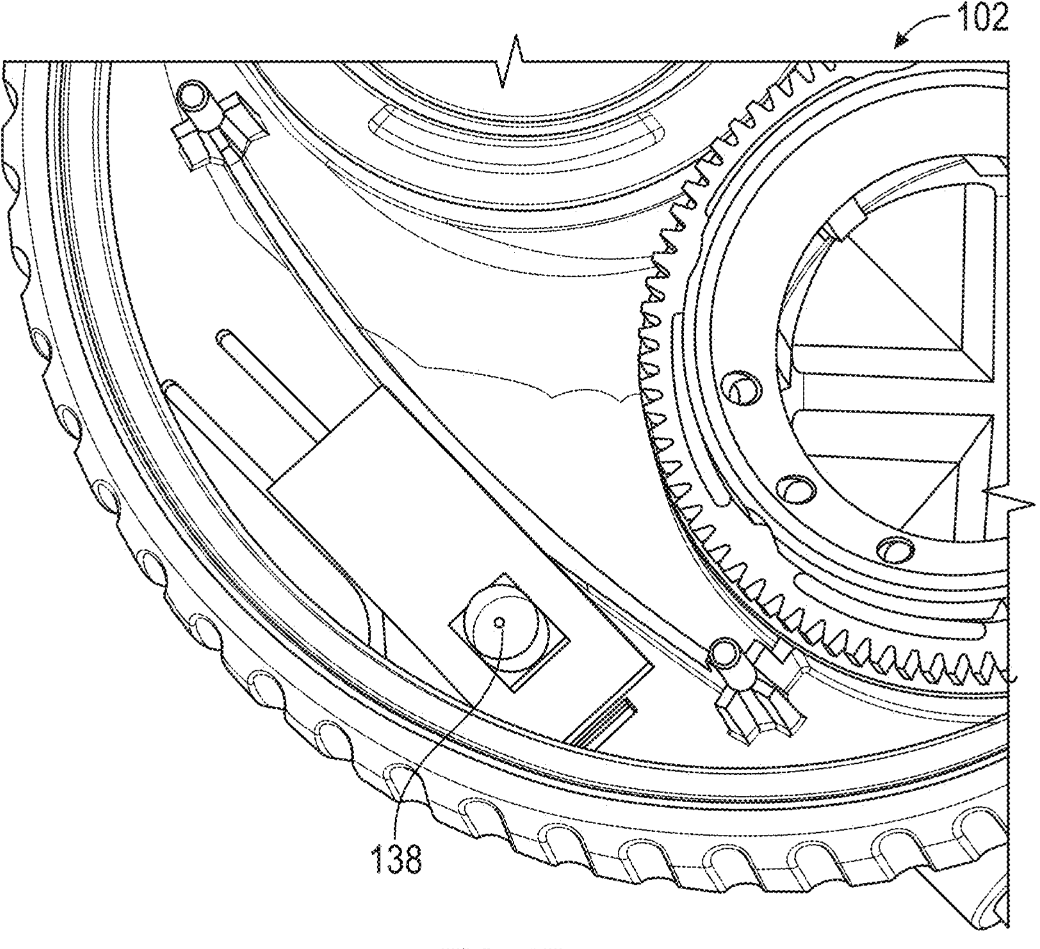
Figure 1F:
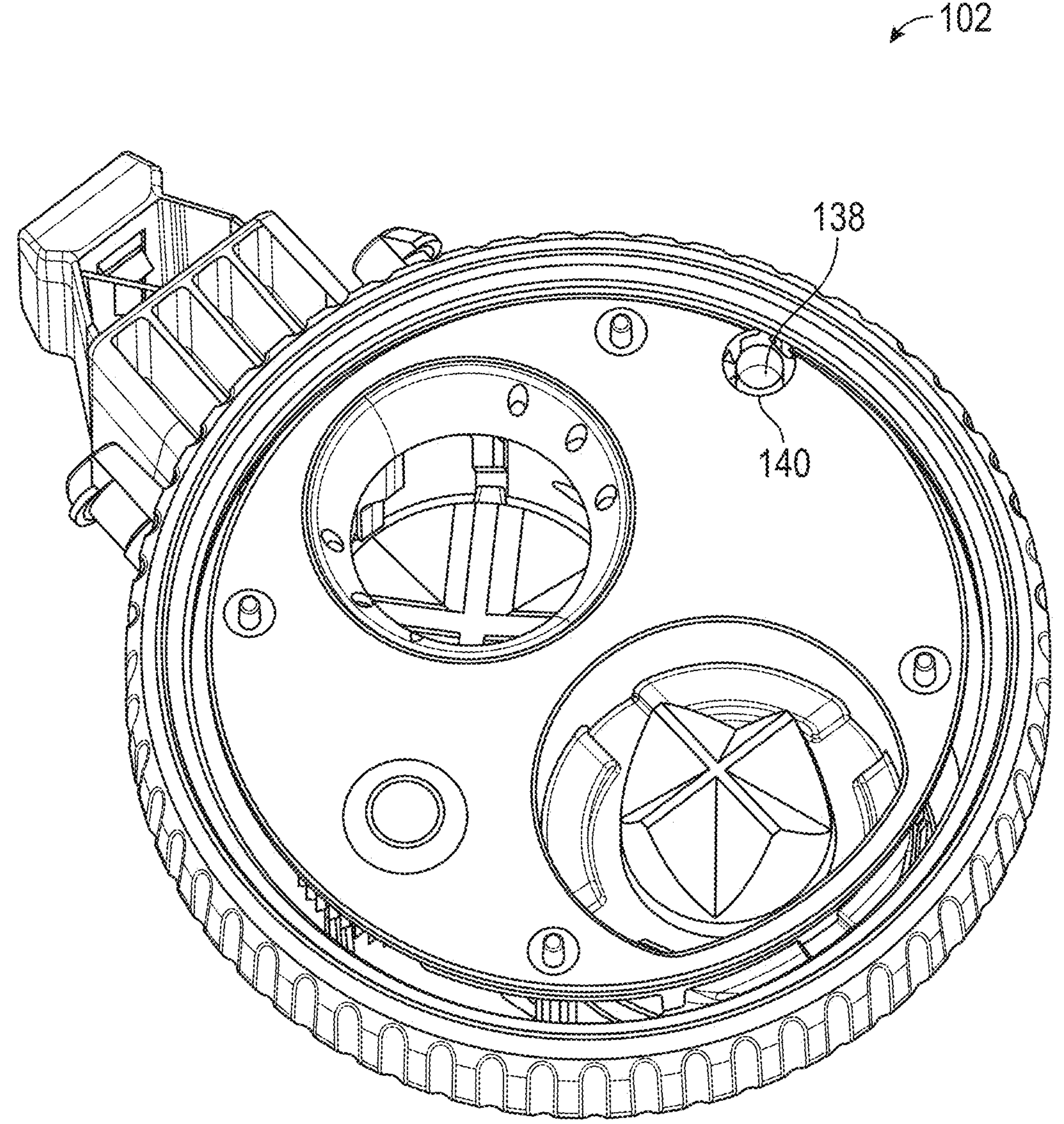

FIGS. 1B-1F depict different views of example instrument seal assembly 102 of instrument access device 100 including one or more integrated lights. In FIG. 1B, instrument seal assembly 102 includes cannula assembly 108, assistant port 120, base 124, pull-tab 128, and button 130. Cannula assembly 108 includes blade 116 and cannula 126. In FIGS. 1C and 1D, integrated into base 124 is circuit 132, switch/relay 134, power source 136, and illumination device 138. FIGS. 1E and 1F depict illumination device 138 mounted within base 124 and positioned so that illumination device 138 is aligned with window/aperture 140 in the bottom (distal) side of base 124.

Referring to FIGS. 1B-1H, base 124 of instrument seal assembly 102 of instrument access device 100 includes illumination device 138, which is configured to provide task lighting within envelope 104 and directed proximally-to-distally generally onto the surgical site sealed by envelope 104 and instrument access device 100. A portion of pull-tab 128 is exposed above the top or proximal end of base 124. The remaining portion of pull-tab 128 can be positioned to break the electrical contact of power source 136. For example, power source 136 can be a one-time use or rechargeable battery and pull-tab 128 can be positioned between the battery contacts and contacts on circuit 132 such that the illumination assembly including circuit 132 and switch 134 is not powered until pull-tab 128 is removed, e.g., by the bedside assistant prior to commencing the surgical procedure.

Also integrated into the proximal end of base 124 is button 130. Button 130 is an example of a user input device by which the user can activate and adjust illumination device 138. Other user input devices may be employed in examples according to this disclosure, including, e.g., a touchscreen, soft keys, trackball, microphone (for audible inputs from user, e.g. voice commands), among other examples. Button 130 is positioned on the proximal end of base 124 adjacent (e.g., over) switch 134. Thus, when button 130 is depressed by a user, the button is deflected to engage and activate switch 134.

Circuit 132 can be a variety of different types of circuits. For example, circuit 132 can include a Printed Circuit Assay (PCA), a Printed Circuit Board (PCB), a Printed Circuit Board Assembly (PCBA), an Integrated Circuit (IC), and an Integrated Circuit Board (ICB), among other examples. Regardless of type, circuit 132 can include one or more processor devices and/or memory devices. For example, circuit 132 can include any one or more of a microprocessor, a controller, a digital signal processor (DSP), an application specific integrated circuit (ASIC), a field-programmable gate array (FPGA), or equivalent discrete or integrated logic circuitry.

Additionally, circuit 132 can include storage media to store and/or retrieve data or other information, for example, signals from switch 134. Storage devices, in some examples, are described as a computer-readable storage medium. In some examples, storage devices include a temporary memory, meaning that a principal purpose of one or more storage devices is not long-term storage. Storage devices are, in some examples, described as a volatile memory, meaning that storage devices do not maintain stored contents when the computer is turned off. Examples of volatile memories include random access memories (RAM), dynamic random access memories (DRAM), static random access memories (SRAM), and other forms of volatile memories known in the art. The data storage devices can be used to store program instructions for execution by processor(s) of circuit 132. The storage devices, for example, are used by software, applications, algorithms, as examples, running on and/or executed by circuit 132. The storage devices can include short-term and/or long-term memory, and can be volatile and/or non-volatile. Examples of non-volatile storage elements include magnetic hard discs, optical discs, floppy discs, flash memories, or forms of electrically programmable memories (EPROM) or electrically erasable and programmable (EEPROM) memories.

As noted, power source 136 can be a variety of one-time use or rechargeable batteries. For example, power source 136 can include a variety of types of batteries used in medical devices, e.g., Zinc-Air, Lithium-Iodide, or a Nickel-Cadmium battery. In other examples, instrument access device 100 can be wired to a dedicated power source, power from which is conditioned to provide power to circuit 132, switch 134, and illumination device 138.

Referring to FIGS. 1E and 1F, illumination device 138 is mounted within base 124 and positioned so that illumination device 138 is aligned with window/aperture 140 in the bottom (distal) side of base 124. Illumination device 138 can include a variety of different types of devices configured to provide illumination. For example, illumination device 138 can be a light emitting diode (LED), which is mounted to circuit 132. Additionally, illumination device 132 can include incandescent, fluorescent, xenon, halogen, including bi-p n halogen, and high-intensity discharge (HID) lamps.

Power source 136 is connected to and powers circuit 132 and illumination device 138. Illumination device 138 is mounted on the distal face of circuit 132. Circuit 132 is connected to and receives signals from switch 134. And, circuit 132 is connected to and is configured to send and receive signals to/from illumination device 138. In an example, a user, e.g., a bedside assistant can activate illumination device 138 to illuminate the surgical site by pressing button 130. In an example, button 130, upon being pressed once by the bedside assistant, will engage switch 134, which can transmit a signal (on/off) to circuit 132. Circuit 132 can, in response to signal(s) from switch 134, cause illumination device 138 to turn on.

In an example, circuit 132 can, in response to a first signal from switch 134, cause illumination device 138 to turn on at a first brightness level. If the bedside assistant presses button 130 a second time, as an example, circuit 132 can cause illumination device 138 to illuminate at a second brightness level. Additionally, if the bedside assistant presses button 130 a third time, circuit 132 can cause illumination device 138 to illuminate at a third brightness level. And, if the bedside assistant presses button 130 a fourth time, circuit 132 can cause illumination device 138 to turn off. In an example, the first brightness level is greater than the second and third brightness levels, the second brightness level is less than the first and greater than the third brightness level.

In addition to modulating the brightness of illumination device 138, circuit 132 and illumination device 138 may be configured to illuminate illumination device 138 in more than one color. For example, depending on the task, background lighting and reflective lighting from a surgical endoscope, it may be beneficial for illumination device 138 to be configured to emit light in the blue and/or red color spectrum. More generally, different light wavelengths may cause less glare or other interferences to user viewing. In examples, illumination device 138 may include multiple lamps or other illumination devices, each of which is configured to emit a different color (wavelength) light. Additionally, instead of modulating the brightness, button 130 (or another button for color) could be employed to modulate the color of light emitted by illumination device 138.

Figure 1G:
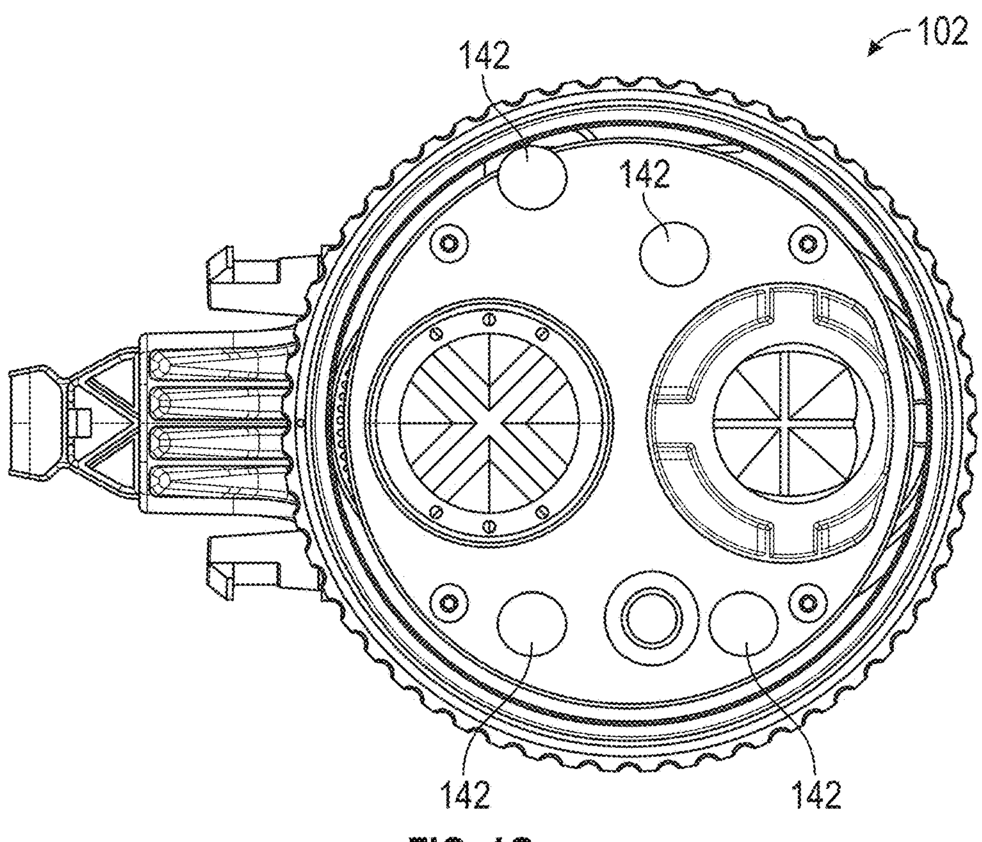
FIG. 1G is a plan view depicting the instrument seal assembly of FIGS. 1A-1F including another example illumination device.
Figure 1H:
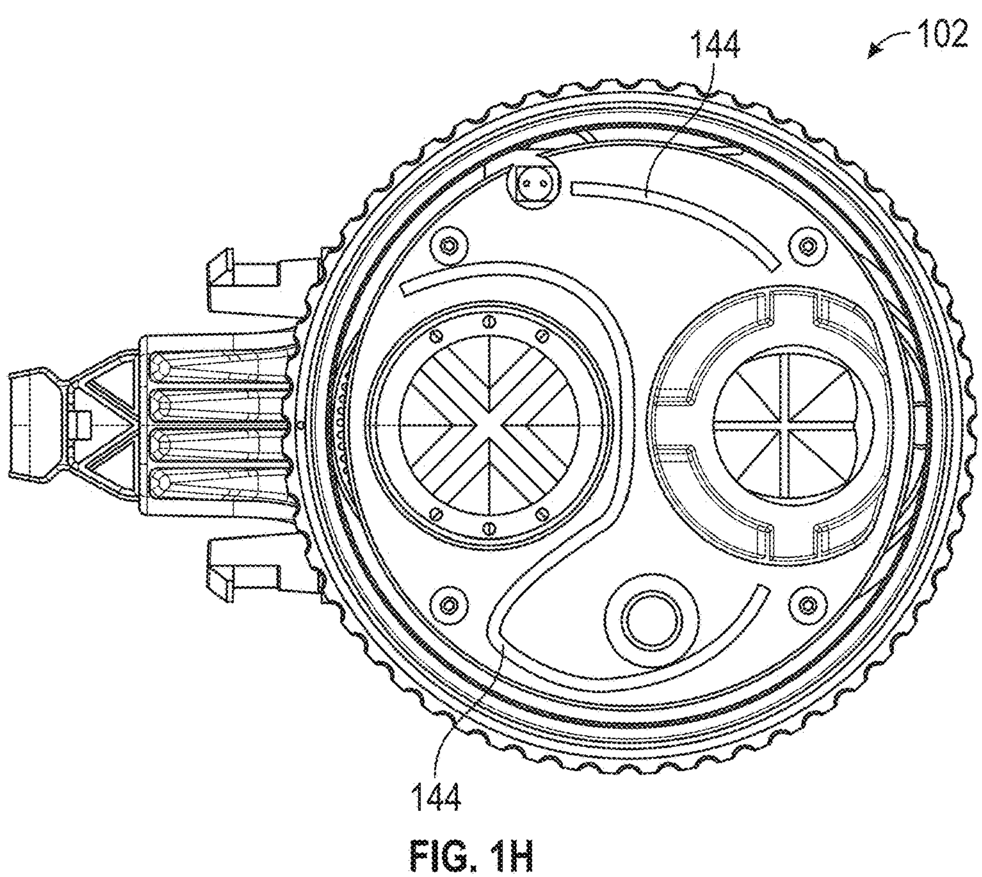
FIG. 1H is a plan view depicting the instrument seal assembly of FIGS. 1A-1F including another example illumination device.
Figure 1I:
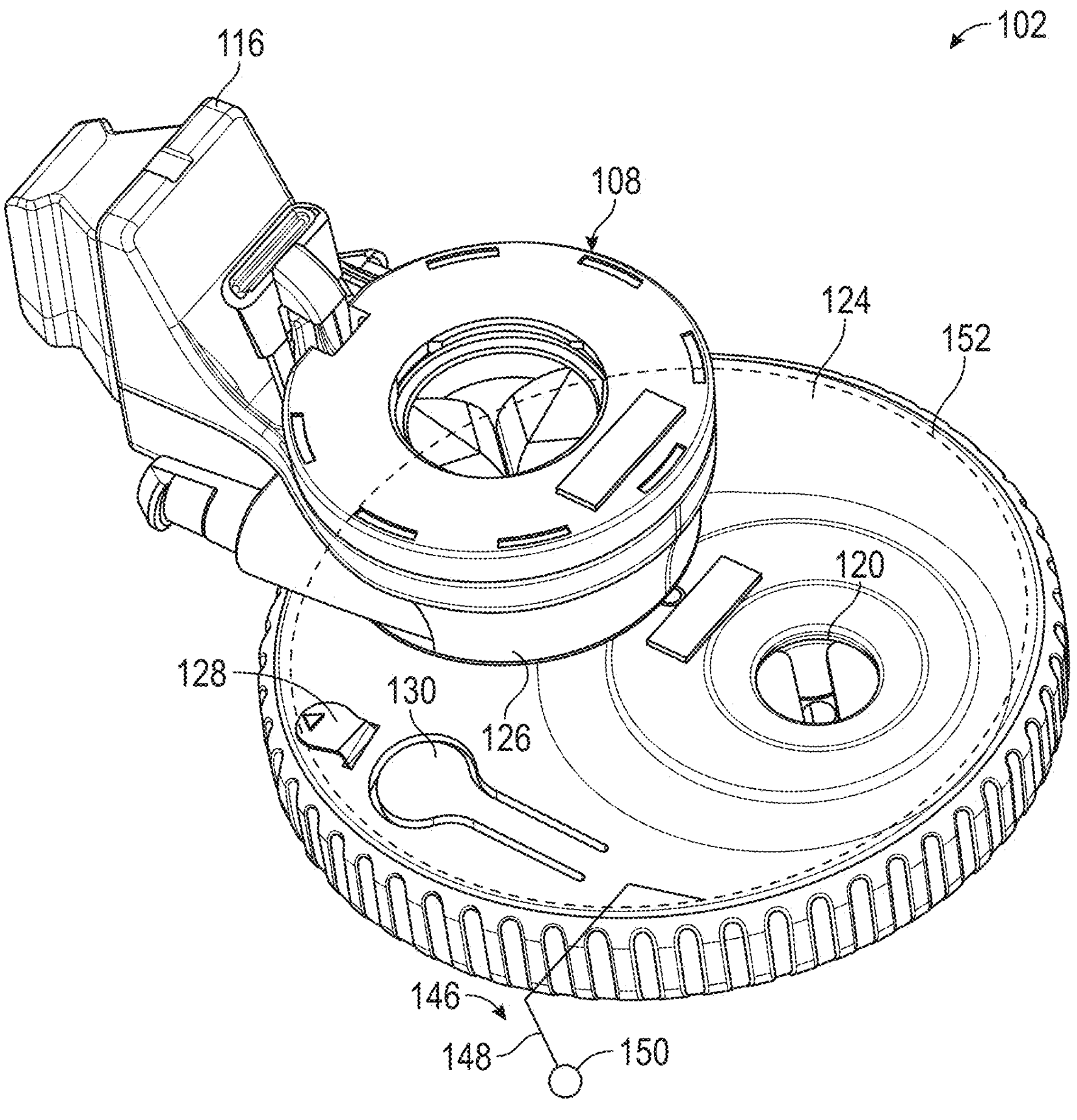
FIG. 1I is a perspective view depicting another instrument seal assembly including an illumination device.

FIG. 1G is a plan view depicting instrument seal assembly 102 including illumination device 142. In this example, illumination device 142 includes a plurality of illumination devices 142, which are distributed over various portions of the distal end of base 124 of instrument seal assembly 102. In the example of FIG. 1G, illumination device 142 includes four illumination devices 142. However, in other examples, a plurality of illumination devices 142 can include fewer or more than four lights. Additionally, illumination devices 142 can be located in a variety of positions in base 124 to improve the level and/or extent of illumination provided by the devices. Illumination devices 142 can include a variety of different types of devices configured to provide illumination. For example, illumination device 142 can be a light emitting diode (LED), which is mounted to circuit 132. Additionally, illumination device 142 can include incandescent, fluorescent, xenon lamps, halogen, and HID lamps, FIG. 1H is a plan view depicting instrument seal assembly 102 including illumination device 144. In this example, illumination device 144 include one or more light pipes. Light pipes are transparent tubes that transmit light from a light source, such as an LED. Designed to carry light short distances with high efficiency, light pipes can bend light around corners and tight spaces delivering excellent visual indication with minimal loss of light intensity. In the example of FIG. 1G, illumination device 144 includes two light pipes. However, in other examples, a plurality of illumination devices 144 can include more than two light pipes. Additionally, illumination devices 144 can be located in a variety of positions in base 124 to improve the level and/or extent of illumination provided by the devices. The light source illuminating the light pipes of illumination device 144 can include a variety of different types of devices configured to provide illumination, including, for example, LED, and incandescent, fluorescent, xenon, halogen, and HID lamps, FIG. 1I is a perspective view depicting instrument seal assembly 102 including illumination device 146 including a flexible and/or articulating arm 148, a lamp 150, and track 152. Arm 148 of illumination device 146 is seated in/moveably coupled to track 152 at a first end of arm 148 and is coupled to lamp 150 at a second end of arm 148. Arm 148 and lamp 150 are configured to be slid or otherwise moved to different positions about the periphery of base 124 of instrument seal assembly 102. Additionally, arm 148 can be flexible and/or articulate to further allow adjustment of the zone/direction that lamp 150 provides task lighting.

As noted above, the examples of FIGS. 1B-1H includes an illumination device coupled to the distal facing surface of base 124 of instrument seal assembly 102 to provide task lighting within envelope 104. In the example of FIG. 1I, however, illumination device 146 is configured to provide task lighting outside of envelope 104. The manually adjustable illumination device 146 may provide a number of advantages relative to the examples of FIGS. 1B-1H, including enabling quick and simple replacement of lamp 150 and enabling adjustment of the task lighting provided by illumination device 146 relative to the orientation of base 124 of instrument seal assembly 102, as base 124 is configured to be rotated during surgical procedures.

Figure 2:
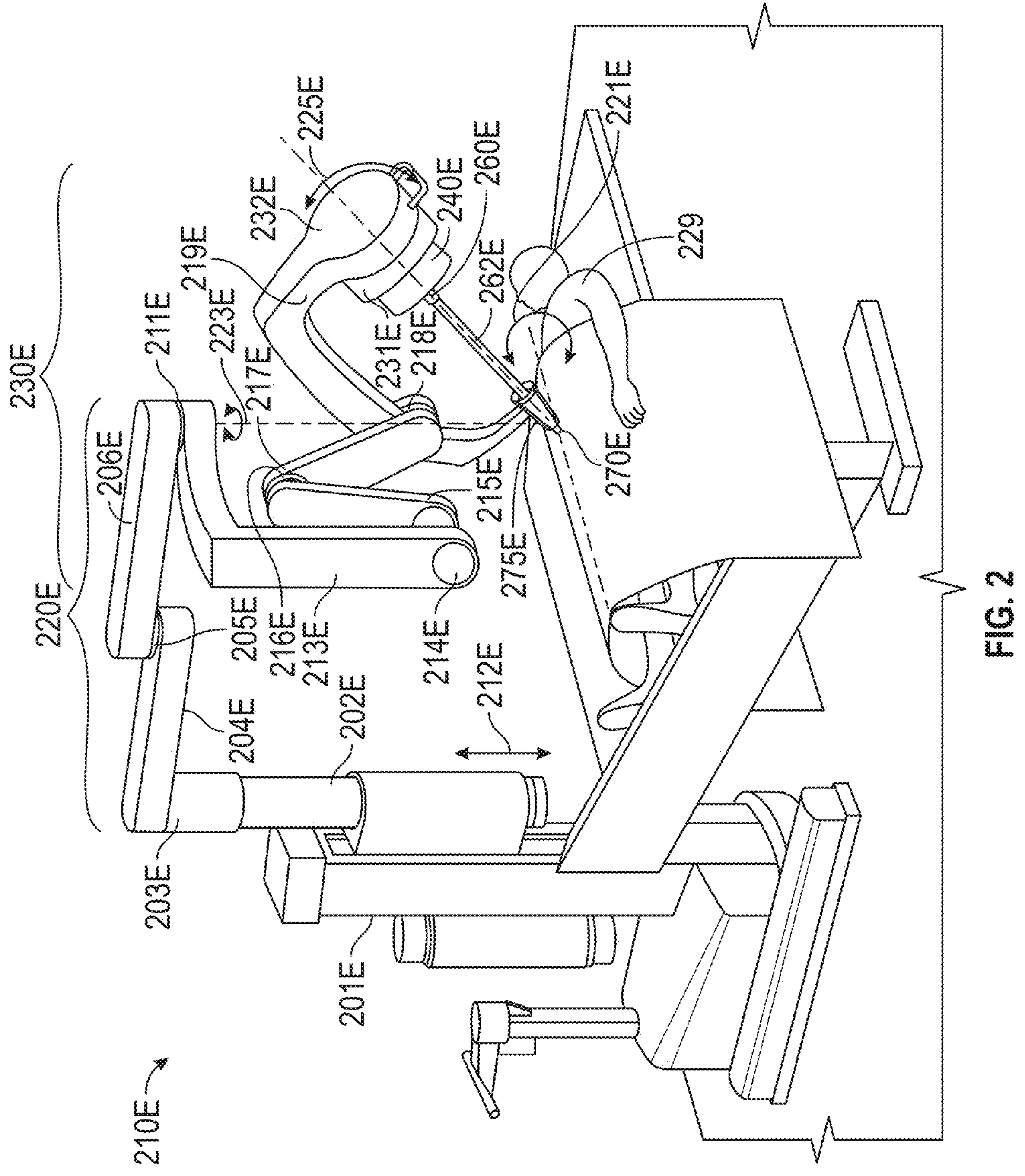
FIG. 2 depicts an example telesurgical system with which an instrument access device with integrated task lighting in accordance with this disclosure may be used.

To illustrate the general context in which an instrument access device in accordance with this disclosure may be used, FIG. 2 provides a schematic perspective view that illustrates aspects of a telesurgical system in accordance with various embodiments. The telesurgical system of FIG. 2 is configured to deliver multiple surgical instruments through a single surgical site (e.g., incision) and using an illuminated instrument access device in accordance with this disclosure and with a multiple instrument entry guide coupled to the access port device.

In general, for the purposes of this description, a telesurgical system includes three main components: an endoscopic imaging system, a user control system (master), and a manipulator system 210E (slave) (shown in FIG. 2), all interconnected by wired (electrical or optical) or wireless connections. One or more data processors (i.e., one or more logical units coupled to one or more memory systems) may be variously located in these main components to provide system functionality. Examples are disclosed in U.S. Pat. No. 9,060,678 (filed Jun. 13, 2007) (disclosing "Minimally Invasive Surgical System"), which is incorporated by reference herein.

The imaging system performs image processing functions on, e.g., captured endoscopic imaging data of the surgical site and/or preoperative or real-time image data from other imaging systems external to the patient. The imaging system outputs processed image data (e.g., images of the surgical site, as well as relevant control and patient information) to a surgeon at user control system. In some aspects, the processed image data is output to an optional external monitor visible to other operating room personnel or to one or more locations remote from the operating room (e.g., a surgeon at another location may monitor the video; live feed video may be used for training; etc.).

The user control system includes multiple-degrees-of-freedom mechanical input devices that allow the surgeon to manipulate the instruments, entry guide(s), and imaging system devices, with computer assistance. These input devices may in some aspects provide haptic feedback from the instruments and surgical device assembly components to the surgeon. The user control system also includes a stereoscopic video output display positioned such that images on the display are generally focused at a distance that corresponds to the surgeon's hands working behind/below the display screen.

Control during insertion and use of the instruments may be accomplished, for example, by the surgeon moving the instruments presented in the image with one or two of the input devices; the surgeon uses the input devices to translate and rotate the instrument in three-dimensional space. Similarly, one or more input devices may be used to translate and rotate the imaging system or an associated surgical device assembly to steer an endoscope or instrument cluster towards a desired location on the output display and to advance inside the patient.

A manipulator system 210E is illustrated in FIG. 2. In the depicted example, the manipulator system 210E is implemented as a patient-side cart, and the surgery is in the abdomen of patient 229. However, the surgical system including manipulator system 210E can be used for a wide variety of surgeries by using various combinations of instruments.

Manipulator system 210E includes a floor-mounted base 201E as shown, or alternately a ceiling-mounted or other mechanically grounded base (not shown). Base 201E may be movable or fixed (e.g., to the floor, ceiling, wall, or other equipment such as an operating table). Base 201E supports the remainder of the manipulator system, which includes a usually passive, uncontrolled manipulator support structure 220E and an actively controlled manipulator system 230E, herein also referred to as entry guide manipulator 230E.

In one example, the manipulator support structure 220E includes a first setup link 202E and two passive rotational setup joints 203E and 205E. Rotational setup joints 203E and 205E allow manual positioning of the coupled setup links 204E and 206E. Alternatively, some of these setup joints may be actively controlled, and more or fewer setup joints may be used in various configurations. Setup joints 203E and 205E and setup links 204E and 206E allow a person to place entry guide manipulator 230E at various positions and orientations in Cartesian x, y, z space. A passive prismatic setup joint (not shown) between link 202E of manipulator support structure 220E and base 201E may be used for large vertical adjustments 212E.

Entry guide manipulator 230E includes an entry guide manipulator assembly 231E that supports a plurality of surgical device assemblies, at least one surgical device assembly being coupled to entry guide manipulator assembly 231E during a surgery. Each surgical device assembly includes a teleoperated manipulator and either a surgical instrument or a camera instrument mounted on the manipulator. For example, in FIG. 2, one surgical device assembly includes, mounted to manipulator 240E, an instrument 260E with a shaft 262E that extends through one of typically multiple channels of entry guide 270E during a surgical procedure.

The procedure conducted on the patient is carried out through a surgical site with an incision near entry guide 270E in the example of FIG. 2. In examples according to this disclosure, the incision in the body wall of the patient can be prepared and dilated by a wound retractor, and a sealed instrument access device can be coupled to the wound retractor. For example, damp 106 of instrument access device 100 can be connected to the wound retractor at the incision site. Instrument access device is configured to receive and seal a cannula of entry guide 270E.

Entry guide manipulator assembly 231E includes an instrument manipulator positioning system (hereinafter simply "positioning system"). The positioning system moves instrument mount interfaces of one or more manipulators 240E in a plane so that, when one or more instruments 260E are coupled to entry guide manipulator assembly 231E using the respective instrument mount interfaces, the shafts of the instruments 260E are each aligned for insertion into one of the channels in entry guide 270E. While the entry guide 270E is depicted as located at a body wall of the patient, it is to be understood that the manipulator system 210E can also be used, without need for modifications, with entry guides located at a distance from the body wall in an entry guide receptacle of an instrument access device as herein described.

The instrument mount interface(s) may be moved into position after attachment of the instrument(s). The plane in which the instrument mount interfaces are moved is generally perpendicular to the lengthwise axis of entry guide 270E, and the trajectories that instrument mount interfaces take in that plane may include straight and/or curved portions in various combinations. As a positioning element of a lateral motion mechanism of the positioning system moves along a trajectory, the instrument mount interface, and effectively a distal tip of a shaft of an instrument coupled to the instrument mount interface, moves along the same trajectory. Thus, motion of the positioning element causes the shaft to be moved to a location where the shaft is aligned with a channel in entry guide 270E. In this position, the shaft can enter and pass through the channel in entry guide 270E without damaging the instrument and without inhibiting operation of the instrument. The particular paths implemented in the positioning system depend at least in part on the types of surgical device assemblies that can be mounted on the entry guide manipulator assembly 231E and/or the configuration of channels in entry guide 270E.

Different entry guides may be used in different surgical procedures. An entry guide that enters the body between the ribs may optionally have a different shape than an entry guide that enters the body through an incision in the abdomen. Further, entry guides that enter the body generally differ, e.g., in length, from entry guides used outside the body, such as entry guides inserted through an entry guide receptacle at a proximal end of an envelope of an instrument access device as disclosed herein; entry guides used outside of and at a distance from the body may be shortened relative to those entering the body. The different shapes of the entry guides require different layouts of the channels that extend through the entry guides, i.e., different channel configurations. Also, the shapes and/or sizes of the shafts of the instruments may be different for different instruments. An entry guide is used that accommodates the shapes and sizes of the shafts of the instruments used in a particular surgical procedure. The trajectories are designed to accommodate a set of entry guides that can be used with manipulator system 210E.

The ability to individually position an instrument, and hence its shaft, with respect to a channel in an entry guide by moving an instrument mount interface provides versatility to manipulator system 210E. For example, this ability allows entry guides with different channel configurations to be used in system 210E. In addition, the positioning system eliminates the need for surgical-procedure-specific instruments. In other words, the instrument manipulator positioning system allows use of a common set of instruments with a variety of entry guides by moving the instrument shafts around, as described above.

Entry guide manipulator 230E includes a kinematic chain of active joints and links that are movable by motors or other actuators and receive movement control signals that are associated with master arm movements at the user control system. Using this kinematic chain, the entry guide manipulator 230E can adjust the position and orientation of the positioning system of entry guide manipulator assembly 231E and, by extension, the instrument. Usually, the entry guide manipulator 230E is configured and operated to constrain rotation of an instrument at a point located on the instrument's shaft, herein referred to as a remote center of motion.

Conventionally, the remote center of motion coincides generally with the position at which an instrument enters the patient (e.g., at the umbilicus for abdominal surgery). In accordance with this disclosure, however, where an instrument access device with an instrument entry guide located outside the body (in a port at the proximal end of the envelope of the instrument access device) is used, the position of the remote center of motion likewise falls outside the body, e.g., slightly above the body wall, and generally along the axis of the entry guide. A remote center of motion above the body wall allows for instruments to be moved radially outward from the entry guide's extended axis proximally of the patient's body wall and so get better triangulation access at or in the incision. Flexible instrument shafts in conjunction with a flexible wound retractor render such flexibility in operating the instruments possible without risking trauma to tissue.

The remote center of motion is the location at which yaw, pitch, and roll axes intersect, i.e., the location at which the kinematic chain of entry guide manipulator 230E remains effectively stationary while joints move through their range of motion. As shown in FIG. 2, a manipulator assembly yaw joint 211E is coupled between an end of setup link 206E and a first end, e.g., a proximal end, of a first manipulator link 213E. Yaw joint 211E allows first manipulator link 213E to move with reference to link 206E in a motion that may be arbitrarily defined as "yaw" around a manipulator assembly yaw axis 223E. As shown, yaw axis 223E of joint 211E is aligned with a remote center of motion located at or near the entry guide 270E.

A distal end of first manipulator link 213E is coupled to a proximal end of a second manipulator link 215E by a first actively controlled rotational joint 214E. A distal end of second manipulator link 215E is coupled to a proximal end of a third manipulator link 217E by a second actively controlled rotational joint 216E. A distal end of third manipulator link 217E is coupled to a fourth manipulator link 219E by a third actively controlled rotational joint 218E; the fourth manipulator link 219E extends in both directions away from the rotational joint 218E and, thus, has two distal ends relative to the location of the joint 218E.

In one embodiment, links 215E, 217E, and 219E are coupled together to act as a coupled motion mechanism. Coupled motion mechanisms are well known (e.g., such mechanisms are known as parallel motion linkages when input and output link motions are kept parallel to each other). For example, if rotational joint 214E is actively rotated, then joints 216E and 218E are also actively rotated so that link 219E moves with a constant relationship to link 215E. Therefore, it can be seen that the rotational axes of joints 214E, 216E, and 218E are parallel. When these axes are perpendicular to yaw axis 223E of joint 211E, links 215E, 217E, and 219E move with reference to link 213E in a motion that may be arbitrarily defined as "pitch" around a manipulator assembly pitch axis. The manipulator pitch axis extends into and out of the page in FIG. 2 at remote center of motion at or near the entry guide 270E. The motion around the manipulator assembly pitch axis is represented by arrow 221E. Since links 215E, 217E, and 219E move as a single assembly in this embodiment, first manipulator link 213E may be considered an active proximal manipulator link, and second through fourth manipulator links 215E, 217E, and 219E may be considered collectively an active distal manipulator link.

An entry guide manipulator assembly platform 232E is coupled to one of the distal ends of fourth manipulator link 219E. Entry guide manipulator assembly 231E is rotatably mounted on platform 232E. Entry guide manipulator assembly 231E can rotate a plurality of surgical device assemblies (e.g., 260E) as a group around axis 225E. Specifically, entry guide manipulator assembly 231E rotates as a single unit with reference to platform 232E in a motion that may be arbitrarily defined as "roll" around an entry guide manipulator assembly roll axis 225E.

In accordance with the present disclosure, all the instruments (including a camera instrument) enter the instrument access device via a single port, which is generally stationary relative to the remote center of motion imposed by entry guide manipulator 230E (and defined by the intersection of manipulator assembly yaw axis 223E, manipulator assembly pitch axis 221E, and manipulator roll axis 225E). The configuration of links 215E, 217E, and 219E, and the configuration of joints 214E, 216E, and 218E are such that remote center of motion is located distal of entry guide manipulator assembly 231E, with sufficient distance to allow entry guide manipulator assembly 231E to move freely with respect to the entry guide 270E.

An entry guide receptacle 275E may be removably coupled (directly or indirectly via a mount) to the distal end of fourth manipulator link 219E opposite the distal end to which entry guide manipulator assembly platform 232E is coupled. In one implementation, the entry guide receptacle 275E or mount is coupled to link 219E by a rotational joint that allows it to move between a stowed position adjacent link 219E and an operational position that ensures that the remote center of motion is located along the entry guide receptacle 275E or the entry guide 270E received therein. During operation, the entry guide receptacle 275E is fixed in position relative to link 219E according to one aspect. Entry guide receptacles and entry guides may be made of various materials, e.g., steel or extruded plastic. Plastic, which is less expensive than steel, may be suitable for one-time use per surgical procedure.

The various passive setup joints/links and active joints/links allow positioning of the instruments and imaging system with a large range of motion when a patient 229 is placed in various positions on a movable table. Certain setup and active joints and links in the manipulator support structure 210E and/or entry guide manipulator 230E may be omitted to reduce the surgical system's size and shape, or joints and links may be added to increase degrees of freedom. It should be understood that the manipulator support structure 210E and entry guide manipulator 230E may include various combinations of links, passive joints, and active joints (redundant degrees of freedom may be provided) to achieve a necessary range of poses for surgery.

The foregoing examples contemplate a "single-port" multiple-instrument access device including integrated task lighting. However, in other examples according to this disclosure, a "multi-port" instrument access device can include similar features as those described above with reference to the "single-port" instrument access device 100. As a reminder, some system architectures enable multiple (e.g., two, three, four, or more) surgical instruments to enter the body through a single body opening (surgical incision or natural orifice), and these systems are sometimes referred to as "single-port" systems. The foregoing examples of FIGS. 1A-1H and FIG. 2 are used in or are so-called "single-port" systems. Other system architectures enable multiple surgical instruments to enter the body individually at corresponding multiple locations, and these systems are sometimes referred to as "mufti-port" systems. A "multi-port" instrument access device with integrated task lighting is included in examples according to this disclosure.

As one example of a "multi-port" application, an instrument access device in accordance with this disclosure includes a gel cap that is configured to be coupled to and seal the proximal opening of a wound retractor. The gel cap comprises a gel pad that acts as an artificial body wall, through which one or more instruments may be inserted into a body cavity, either directly or through one or more trocars. The gel pad can permit flexible instrument placement, as well as translational and angular degrees of freedom for the instruments while maintaining a gas tight seal. Such an example gel cap instrument access device could include integrated task lighting in a similar manner as the examples described above. For example, one or more illumination devices can be incorporated into a housing or other structure of the gel cap that is proximally-to-distally facing, so that the illumination device(s) are generally arranged to illuminate portions or all of the incision/surgical site on which the gel cap is employed.

The foregoing examples include example illumination devices, which are powered by a power source like, for example, a one-time use or rechargeable battery. However, other example instrument access devices in accordance with this disclosure may include self-contained, short-term illumination devices, including devices that provide illumination by chemiluminescence. So called "glow sticks" are a familiar example of this type of illumination device. A glow stick is a self-contained, short-term light-source, which includes a translucent plastic tube containing isolated substances that, when combined, make light through chemiluminescence (does not require an external energy source). An illumination device employing chemiluminescence could be integrated into an instrument access device in accordance with this disclosure and could be configured such that a user, e.g., bedside assistant could rupture the barrier separating the two chemicals upon commencement of the procedure to provide task lighting to the surgical site from there on.

Persons of skill in the art will understand that any of the features described above may be combined with any of the other example features, as long as the features are not mutually exclusive. All possible combinations of features are contemplated, depending on clinical or other design requirements. In addition, if manipulating system units are combined into a single system (e.g., telesurgery system), each individual unit may have the same configuration of features, or, one patient-side unit may have one configuration of features and another patient-side unit may have a second, different configuration of features.

The examples (e.g., methods, systems, or devices) described herein may be applicable to surgical procedures, non-surgical medical procedures, diagnostic procedures, cosmetic procedures, and non-medical procedures or applications. The examples may also be applicable for training, or for obtaining information, such as imaging procedures. The examples may be applicable to handling of tissue that has been removed from human or animal anatomies and will not be returned to a human or animal, or for use with human or animal cadavers. The examples may be used for industrial applications, general robotic uses, manipulation of non-tissue work pieces, as part of an artificial intelligence system, or in a transportation system.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. But, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. Coordinate systems or reference frames are provided for aiding explanation, and implantations may use other reference frames or coordinate systems other than those described herein.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The claimed invention is:

1. An instrument access device comprising:

an envelope comprising a distal end, a proximal end, a cavity between the distal and proximal ends, and an opening at the proximal end; and an instrument seal assembly coupled to the proximal end and configured to seal the opening, the instrument seal assembly comprising a base, a track in the base, and an illumination device movably connected to the track and configured to illuminate a zone of the distal end of the envelope, the illumination device comprising an arm and a lamp, the arm being moveably coupled to the track in the base at a first end and coupled to the lamp at a second end of the arm, and in addition to being movably coupled to the track, the arm being articulable to change the zone illuminated by the lamp.

2. The instrument access device of claim 1, wherein the instrument seal assembly comprises a single instrument access port.

3. The instrument access device of claim 1, wherein the instrument seal assembly comprises a plurality of instrument access ports.

4. The instrument access device of claim 1, wherein the lamp of the illumination device comprises a light emitting diode, an incandescent lamp, a fluorescent lamp, xenon lamp, a halogen lamp, a high-intensity discharge lamp, or a chemiluminescence illumination component.

5. The instrument access device of claim 1, further comprising:

a user input device configured to activate and deactivate the illumination device, wherein actuation of the user input device a first time causes the lamp of the illumination device to illuminate the zone of the distal end of the envelope at a first brightness, and wherein actuation of the user input device a second time after the first time causes the lamp of the illumination device to illuminate the zone of the distal end of the envelope at a second brightness different than the first brightness.

6. The instrument access device of claim 5, wherein actuation of the user input device a subsequent time after the second time causes the lamp of the illumination device to deactivate.

7. A medical device comprising:

means for covering a proximal opening of a wound retractor, the means for covering comprising means for introducing one or more instruments through the means for covering and means for sealing the proximal opening of the wound retractor, the means for sealing comprising a base and a track in the base; and an illumination device movably connected to the track and configured to illuminate a zone of a distal end of the means for covering, the illumination device comprising an arm and a lamp, the arm being moveably coupled to the track in the base at a first end and coupled to the lamp at a second end of the arm.

8. The medical device of claim 7, wherein the illumination device is configured to illuminate a zone within a perimeter of the wound retractor.

9. The medical device of claim 7, wherein:

the means for covering comprises means for connecting the means for covering to the wound retractor and means for defining an enclosed space;

the means for defining an enclosed space is connected to and between the means for connecting and the means for sealing; and the means for sealing comprises the means for illuminating.

10. The medical device of claim 9, wherein:

the means for sealing comprises an instrument seal assembly; and the instrument seal assembly comprises the base and one or more instrument access ports.

11. The medical device of claim 9, wherein:

the means for defining an enclosed space comprises an envelope having proximal and distal openings;

the means for sealing is in the proximal opening of the envelope; and the means for connecting is in the distal opening of the envelope.

12. The medical device of claim 7, further comprising:

means for activating and deactivating the illumination device, wherein the means for activating and deactivating comprises a user input device on the means for covering, and wherein the means for activating and deactivating comprises means for causing the illumination device to illuminate the zone at a first brightness and at a second brightness different from the first brightness.

13. The medical device of claim 7, wherein, in addition to being movably coupled to the track, the arm is articulable to change the zone illuminated by the illumination device.

* * * * *